US006801808B2

(12) United States Patent
Lee

(10) Patent No.: US 6,801,808 B2
(45) Date of Patent: Oct. 5, 2004

(54) TISSUE TENSIONING ELECTROTHERAPY DEVICE

(76) Inventor: Justin J. Lee, 13121 Briarwood St., Cerritos, CA (US) 90703

(*) Notice: Subject to any disclaimer, the term of this patent is extended or adjusted under 35 U.S.C. 154(b) by 366 days.

(21) Appl. No.: 10/076,002

(22) Filed: Feb. 14, 2002

(65) Prior Publication Data

US 2002/0072771 A1 Jun. 13, 2002

Related U.S. Application Data

(63) Continuation-in-part of application No. 09/585,507, filed on Jun. 1, 2000.

(51) Int. Cl.$^7$ .............................. A61N 1/18; A61N 1/32
(52) U.S. Cl. ...................... 607/76; 607/115; 607/145; 607/150; 607/151
(58) Field of Search .............................. 607/76, 5, 115, 607/145, 150, 151

(56) References Cited

U.S. PATENT DOCUMENTS

| | | | |
|---|---|---|---|
| 4,033,356 A | 7/1977 | Hara | 607/152 |
| 4,510,939 A | 4/1985 | Brenman et al. | 600/384 |
| 4,920,981 A | 5/1990 | Dervieux | 607/145 |
| 4,957,480 A | 9/1990 | Morenings | 604/20 |
| 5,203,349 A | 4/1993 | Kogan | 607/145 |
| 5,304,207 A | 4/1994 | Stromer | 607/3 |
| 5,365,926 A | 11/1994 | Desai | 600/374 |
| 5,385,530 A | 1/1995 | Wu | 601/21 |
| 5,470,349 A | 11/1995 | Kleditsch et al. | 607/75 |
| 5,527,357 A | 6/1996 | Springer, Jr. | 607/140 |
| 5,607,461 A | 3/1997 | Lathrop | 607/75 |
| 5,620,483 A | 4/1997 | Minogue | 600/115 |
| 5,730,128 A | 3/1998 | Pomeranz et al. | 600/374 |
| 5,948,011 A | 9/1999 | Knowlton | 607/101 |
| 6,283,988 B1 | 9/2001 | Laufer et al. | 607/96 |
| 6,321,113 B1 * | 11/2001 | Parker et al. | 607/5 |
| 6,458,121 B1 * | 10/2002 | Rosenstock et al. | 606/34 |

* cited by examiner

*Primary Examiner*—Carl Layno
(74) *Attorney, Agent, or Firm*—Stetina Brunda Garred & Brucker

(57) ABSTRACT

A tissue tensioning electrostimulator device. The device includes a plurality of laterally separable electrodes for placement against bodily tissue and for discharging electric current thereon. The device also includes a power circuit in electrical communication with the electrodes and electrically connectable to a power supply for energizing the electrodes. The device also includes stored electrotherapy regimens based on user characteristics. The device also includes a microprocessor having logic for selecting an electrotherapy regimen for a user of the tissue tensioning electrostimulator device based on characteristics of the user of the tissue tensioning electrostimulator device.

12 Claims, 4 Drawing Sheets

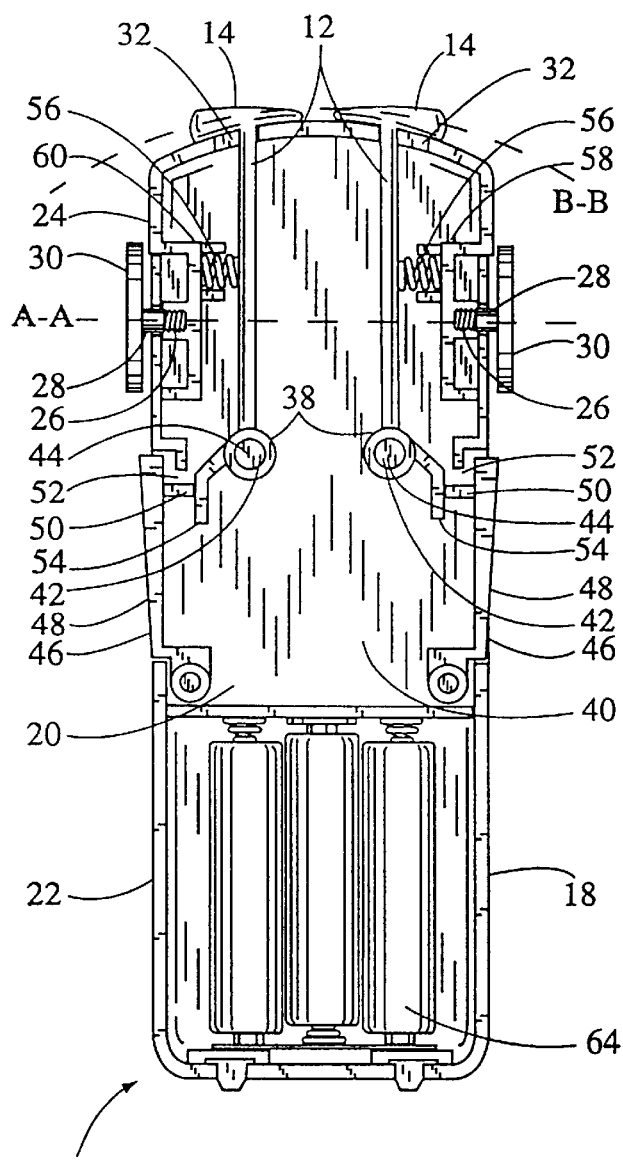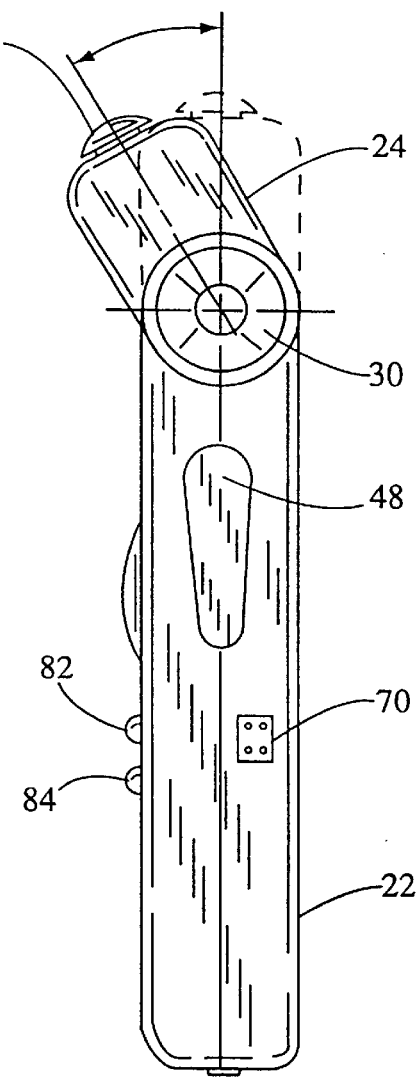
Fig. 4
Fig. 5

| SELECT USER CHARACTERISTICS |
|---|

GENDER:
MALE    FEMALE

RACE:
CAUCASIAN    BLACK    HISPANIC    ASIAN    NO ANSWER

SKIN TYPE:
OILY    NORMAL    DRY

AGE GROUP:
20-29    30-39    40-49    50-59    60+

SELECT AREA FOR THERAPY
EYES    NOSE    CHEEKBONES    MOUTH    CHIN
UPPER ARM    STOMACH    THIGHS

TISSUE TENSIONING ELECTROTHERAPY DEVICE

CROSS-REFERENCE TO RELATED APPLICATIONS

This application is a continuation-in-part of U. S. application Ser. No. 09/585,507, filed Jun. 1, 2000, the entire contents of which are incorporated by reference herein.

STATEMENT RE: FEDERALLY SPONSORED RESEARCH/DEVELOPMENT (Not Applicable)

BACKGROUND OF THE INVENTION

The present invention relates generally to electrotherapy devices, and more particularly to an electrotherapy device which places bodily tissue in tension and applies an electric current to the tissue while it is in tension. The disclosure herein is primarily directed to an electrotherapy device for applying electric current to skin tissue, however, the device also has utility for applying electric current to other types of human or animal tissue.

Topically applied electric current, or electrotherapy, is a well known technique for treating a variety of medical conditions. For example, as disclosed in Kogan (U.S. Pat. No. 5,203,349) and Stromer (U.S. Pat. No. 5,304,207), electrotherapy can be useful for treating pain because it is believed that electric current interrupts pain signals transmitted by the nervous system. Lathrop (U.S. Pat. No. 5,607,461) also discloses that topically applied electric current can be useful for the treatment of lesions caused by the herpes simplex virus. In addition, Springer, Jr. (U.S. Pat. No. 5,527,357) discloses that electric current, when applied to certain points on the face of a patient, can be used to train and condition facial muscles for improved facial skin tone.

Electrotherapy typically involves placement of one or more electrodes adjacent to the skin or tissue of a patient. For many electrotherapy procedures, the actual target for the electric current is often disposed below the surface of the tissue. For instance, facial muscles are the target for the skin toning procedure disclosed in Springer. Likewise, nerves are the target for the pain treatment therapies described in Stromer and Kogan. Consequently, it is critical that the electric current reaches the intended target. In addition, sufficient current must arrive at the target site and the current must have an adequate energy level to produce the desired response.

While there are a number of electrotherapy techniques and devices in the prior art, current electrotherapy procedures can be less effective because some or all of the electricity propagates laterally across the tissue surface rather than into the depth of the tissue. During electrotherapy, the contour of the tissue surface can significantly influence propagation of the electric current. For example, on a wrinkled surface, adjacent areas of the tissue are folded in close proximity to the contact point of the electrodes. As a result, electricity may jump to the adjacent surface tissue rather than penetrate into the tissue depth. This tendency can be aggravated if the adjacent tissue surface is in contact with the target area, or if electrolytic fluids, such as perspiration and skin oils, are present within the wrinkle crevices. In addition, some electrotherapy procedures require the application of electrolytes to the target surface, and over-application of the electrolytes can encourage the electricity to propagate laterally.

Wrinkles and folds in the tissue surface can also increase the electrical resistance between the electrode and the underlying target. In many cases, the electrodes are larger than the span of wrinkle crevices, and the electrodes will normally seat atop the crests in the tissue surface. Consequently, there will be a greater depth of tissue material, and therefore greater electrical resistance, between the electrode and the underlying target. In these circumstances, the electric current is discouraged from penetrating towards the target, and a greater voltage may be required to ensure that the underlying target is sufficiently energized.

In view of the above considerations, a primary object of the present invention is to provide an electrotherapy device which separates wrinkled and folded tissue for application of an electric current thereon.

Another object of the present invention is to provide an electrotherapy device in which the electrodes can be easily manipulated for tensioning the tissue surface and separating wrinkled and folded tissue.

Still another object of the present invention is to provide an electrotherapy device which is portable and can be operated with one hand.

Yet another object of the present invention is to provide an electrotherapy device which has pivotally adjustable electrodes for advantageous placement of the electrodes against the skin of a patient.

These and other objects of the present invention will become apparent throughout the description thereof which now follows.

SUMMARY OF THE PRESENT INVENTION

The present invention is a tissue tensioning electrostimulator device. The device includes a plurality of laterally separable electrodes for placement against bodily tissue and for discharging electric current thereon. The device also includes a power circuit in electrical communication with the electrodes and electrically connectable to a power supply for energizing the electrodes. In the preferred embodiment, the device also has an adjuster for laterally moving the electrodes.

In exemplary embodiments, the device also stores instructions for electrotherapy regimens based on characteristics of the user. The device may also include a microprocessor having instructions for selecting instructions for an electrotherapy regimen based on characteristics of the user of the tissue tensioning electrostimulator device.

The power circuit can be configured to engage a battery power supply or an alternating current supply. For battery operation, the power circuit can include an inverter for converting direct current power to alternating current power, and a selectively adjustable frequency regulator for regulating the discharge current frequency. For operation with an alternating current power source, the power circuit can be provided with a power conditioner for regulating the voltage and amperage of the discharge current, and a selectively adjustable frequency regulator for regulating the frequency of the discharge current.

The device can also be provided with a hand held, hollow casing for mounting the electrodes, adjuster, and power circuit therein. The casing can include a hollow body portion and a hollow head portion from which the electrodes extend. In the preferred embodiment, the head portion is rotatably mounted to the body portion.

The tissue tensioning device here taught thus separates wrinkled and folded tissue while discharging an electric current thereon. In addition, the device can be provided with a hand held casing and an adjuster so that the electrodes can be easily manipulated for tensioning the skin and separating wrinkled and folded tissue. Furthermore, the casing has a rotatable head portion to facilitate convenient placement of the electrodes upon bodily tissue.

BRIEF DESCRIPTION OF THE DRAWINGS

An illustrative and presently preferred embodiment of the present invention is shown in the accompanying drawings in which:

FIG. 4 is a frontal cross-sectional view of the device of FIG. 1;

FIG. 5 is a side view of the device of FIG. 1;

DETAILED DESCRIPTION OF THE PREFERRED EMBODIMENT

Figure 1:
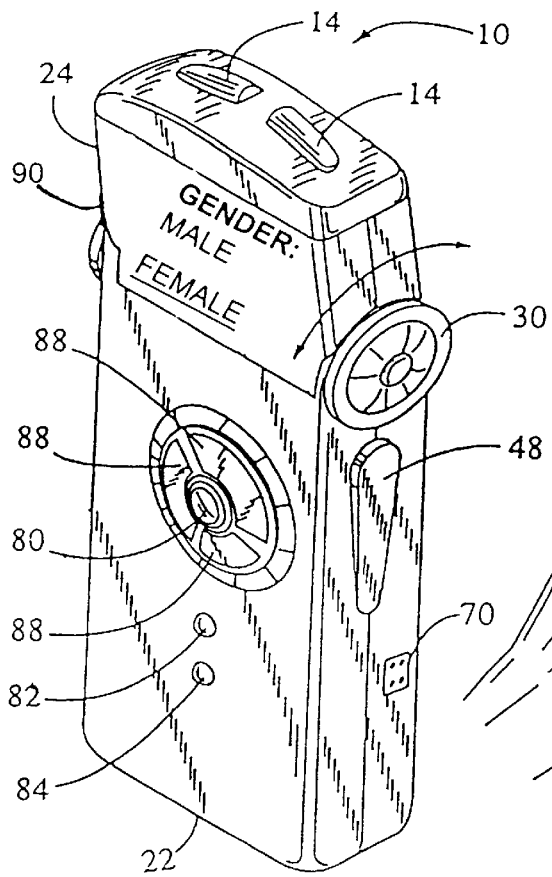
FIG. 1 is a perspective view of a tissue tensioning electrotherapy device.
Figure 6:
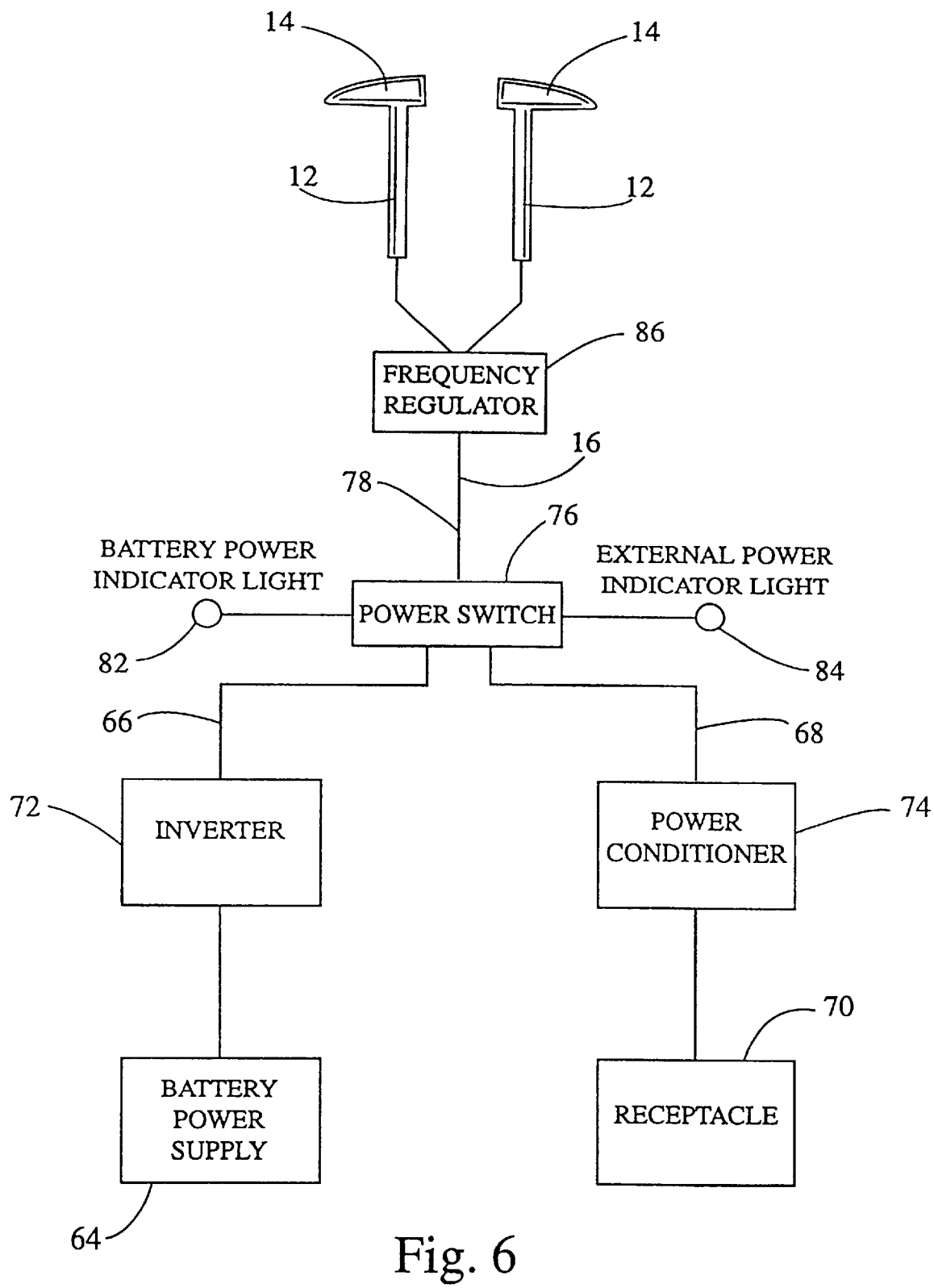
FIG. 6 is a schematic of the electrical circuitry for the device of FIG. 1.

Referring to FIGS. 1 and 4, a tissue tensioning electrotherapy device 10 is illustrated. The tissue tensioning electrotherapy device can be held and operated using one hand, thus allowing a user to self-administer the tissue tensioning electrotherapy. The device 10 includes a pair of laterally separable electrodes 12, that is, the discharge ends 14 of the electrodes 12 are fixed within a common plane of motion, and the discharge ends 14 are free to move away from each other within that plane. The electrodes 12 can be flexibly joined together for lateral separation within a common plane, or the electrodes 12 can be mounted to a separate mounting structure. As shown in FIG. 6, the device 10 also includes a power circuit 16 electrically connected to the electrodes 12 and electrically engageable with a power supply for energizing the electrodes 12.

Figure 2:
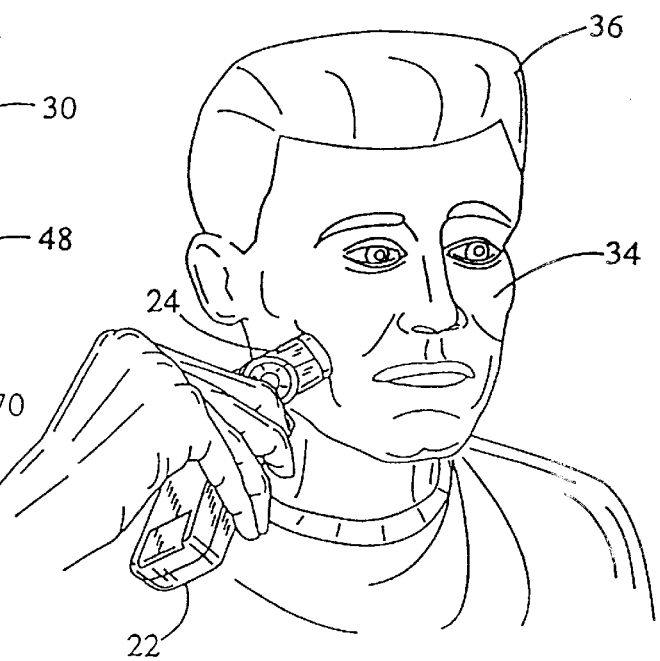
FIG. 2 is a perspective view of the device of FIG. 1 placed against the facial tissue of a patient.

Referring to FIGS. 2 and 4, the device 10 can be provided with a mounting structure, which in the preferred embodiment is a non-conductive casing 18 having an interior chamber 20 within which the electrodes 12 and power circuit 16 can be mounted. The casing 18 can include a body portion 22 and a head portion 24 rotatably attached to the body portion 22. For this type of attachment, the head portion 24 can be formed with a pair of opposed, threaded axle holes 26 and the body portion 22 can be formed with a pair of opposed axle holes 28 disposed for alignment with the threaded axle holes 26 about an axis A—A. With this configuration, the head portion 24 and body portion 22 can be rotatably connected by inserting a pair of threaded cylindrical axles 30 through the body axle holes 28, and then engaging the threaded axles 30 within the threaded axle holes 26 of the head portion 24.

Referring again to FIGS. 2 and 4, the head portion 24 also has a pair of laterally extending slots 32 sized to allow passage of the electrodes 12 therethrough and to permit lateral motion of the electrodes 12. With this arrangement, the electrodes 12 can be placed opposite the tissue 34 of a patient 36 by positioning the head portion 24 adjacent to the tissue 34. As particularly shown in FIG. 2, the head portion 24 can also be rotated to obtain a convenient orientation for placement against the tissue 34.

Figure 3:
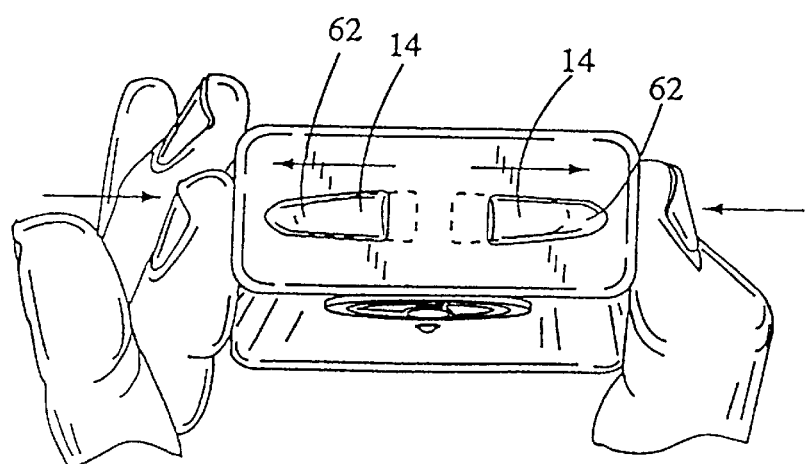
FIG. 3 is a plan view of the device of FIG. 1 showing a pair of oscillating electrodes.

Referring to FIGS. 3 and 4, the rear portion 38 of the electrodes 12 can be rotatably mounted to an interior wall 40 of the casing 18. For this type of mounting, the rear portion 38 of each electrode 12 can be formed with an aperture 42 for receiving respective ones of a pair of parallel mounting posts 44 extending from the interior wall 40. The length of the posts 44 and the depth of the chamber 20 can be selected to prevent the electrodes 12 from coming off the posts 44. When fixed in this manner, the electrodes 12 are restricted to movement within a common plane B—B. In this particular embodiment, the electrodes 12 are also restricted to co-linear movement within the plane B—B. It is recognized, of course, that the electrodes 12 can be mounted by other methods and for other types of motion within a common plane. For example, the posts 44 can be oriented in non-parallel relationship to each other so the electrodes 12 travel at an angle to each other. Moreover, three or more electrodes 12 can be so mounted for movement within a common plane. Alternatively, the rear portion 38 of the electrodes 12 can be provided with an axle projection rotatable within a recess disposed in the interior wall 40 of the casing 18.

Referring again to FIGS. 3 and 4, the device 10 can be provided with an adjuster 46 for laterally moving the electrodes 12. As particularly shown in FIG. 4, the adjuster 46 can include a pair of grip buttons 48 rotatably mounted to the casing 18 and each having an attached linkage arm 50. The linkage arms 50 extend through respective passages 52 in the body portion 22 of the casing 18 for engaging respective ones of the electrodes 12. When this type of adjuster is employed, the electrodes 12 can be provided with a lever extension 54 for engaging the linkage arm 50. The contact point between the extension 54 and linkage arm 50 is disposed on the opposite side of the electrode rotational axis relative to the discharge end 14 of the electrode 12. In this manner, depressing one or both of the grip buttons 48 separates the discharge ends 14 of the electrodes 12. Thus, when the discharge ends 14 are placed against the tissue 34 of the patient 36, the electrodes 12 can be manipulated for placing the tissue 34 in moderate tension and thereby separating folds and wrinkles in the surface of the tissue 34. Since the tissue tensioning electrotherapy device 10 can be held and operated with one hand, the user can use his or her second (free) hand to manipulate the skin to achieve the desired tissue tension.

Referring again to FIG. 4, the adjustor 46 can also include a pair of springs 56 each attached to respective ones of the electrodes 12 and to respective ones of the right interior wall 58 and left interior wall 60 of the head portion 24. The length of the spring is sized to force the electrodes 12 into a minimally separated position when the grip buttons 48 are released. This position is defined by the size of the slots 32. It is recognized, of course, that other types of adjustors can also be employed. For example, the adjuster may comprise a pair of rotatably mounted, cam shaped thumb dials disposed to contact respective ones of the lever extensions 54 such that rotation of the dials correspondingly rotates the electrodes 12.

Referring to FIG. 3, the discharge ends 14 of the electrodes 12 can be formed in a generally oval shape to minimize pinching of the tissue 34 when the electrodes 12 separate. In addition, the exterior surface 62 of the electrodes 12 can be smoothed and rounded so that movement of the electrodes 12 is less likely to scratch or cut the target tissue.

The electrodes 12 can be constructed from any conductive material such as copper, iron, and aluminum The electrodes 12 should also be constructed with sufficient stiffness for manipulating the tissue surface. In addition, when the device 10 is provided with a rotatable casing, the electrodes 12 should also be shaped and constructed to flex in unison with the head portion 24.

Referring to FIG. 6, the power circuit 16 is electrically connected to the electrodes 12 and electrically engageable with a power supply. In the preferred embodiment, the device 10 includes an internally mounted battery power supply 64, and the power circuit 16 has a first branch 66 electrically connected to the battery power supply 64. The power circuit 64 also has a second branch 68 electrically connected to an external power receptacle 70 disposed in the body portion 22 of the casing 18. The battery power supply 64 can be three 1.5 volt AAA batteries connected in series to obtain a 4.5 voltage differential. The receptacle 70 can be configured for receiving and electrically engaging a standard plug (not shown) disposed on one end of a standard electrical cord (not shown). The opposite end of the cord can then be engaged with an alternating current power source such as a standard home or office wall outlet (not shown).

Referring to FIG. 6, the first branch 66 can include a standard inverter circuit 72 for converting direct current power to alternating current power. The second branch 68 of the power circuit 16 can include a standard power conditioning, or rectifying, circuit 74 for regulating the voltage and amperage of the alternating current discharged by the electrodes 12. The first branch 66 and second branch 68 are electrically connected to a power switch 76, and the switch 76 is electrically connected to the electrodes 12 by the main branch 78 of the power circuit 16. In the preferred embodiment, the switch 76 has three operating states: a first position for disconnecting the main branch 78 from the first and second branches 66, 68 to de-energize the electrodes 12, a second position for electrically connecting the main branch 78 with the first branch 66 to energize the electrodes 12 from the battery power supply 64, and a third position for electrically connecting the main branch 78 with the second branch 68 to energize the electrodes 12 from an external power source.

Referring to FIGS. 1 and 6, the switch 76 can be provided with a standard push button operator 80 for selectively positioning the power switch 76 in the respective states. The operator 80 advances the switch from one position to the next in a repeating cycle. The switch 76 can also be provided with a battery indicator light 82 and an external power light 84 which respectively illuminate to indicate that the device 10 is battery powered or energized from an external power source. For this switch configuration, the casing 18 can be provided with an opening (not shown) for exposing the push button operator 80 and two holes (not shown) for exposing the battery indicator light 82 and the external power light 84.

Referring again to FIG. 6, the main branch 78 of the power circuit 16 can include a frequency regulator 86 for selectively regulating the frequency of the discharge current. The frequency regulator 86 can be a standard frequency regulation circuit. In the preferred embodiment, the frequency regulator 86 is adjustable to three discharge current frequency settings: low frequency, mid-range frequency, and high frequency. Referring back to FIG. 1, the frequency regulator 86 can be provided with three standard push button operators 88, each associated with respective ones of the frequency settings. The casing 18 can also be provided with three apertures (not shown) for exposing the push button operators 88. In this manner, a user can select the desired discharge current frequency by pressing the appropriate push button operator 88. It is recognized, of course, that the frequency regulator 86 can be configured to permit other ranges of frequency adjustment. For example, the frequency regulator 86 can be configured for incremental frequency adjustment with a dial adjustment mechanism.

It is also recognized that the device 10 can be configured to operate exclusively from battery power, or exclusively from an alternating current power source. If the device 10 is configured for battery operation alone, the second branch 68 of the power circuit 16 can be eliminated, and the first branch 66 could be configured to engage either an internal or external battery power supply. In addition, the frequency regulator and inverter can be combined within a standard variable frequency output inverter circuit. The switch 76 would also be configured with two operating states: a first position for energizing the electrodes 12 from the battery power supply, and a second position for de-energizing the electrodes 12. Likewise, the switch 76 would only require one light to indicate that the device 10 is energized.

Similarly, the first branch 66 would be eliminated if the device 10 is configured to operate exclusively from an alternating current power supply. The switch 76 would again be configured with two operating states: a first state for energizing the electrodes 12 from the alternating current power supply, and a second state for de-energizing the electrodes 12. In addition, the switch 76 would only require one light to indicate that the device 10 is energized.

It is likewise recognized that the device 10 can be configured to discharge direct current power exclusively or as an alternative to alternating current. If the device 10 will exclusively discharge direct current, the power circuit 16 can be configured so the electrodes 12 are in direct electrical communication with either an internally mounted battery power supply or with an external battery power supply. For this mode of operation, the power circuit 16 could also include a dual state power switch for energizing and de-energizing the electrodes 12. The power circuit 16 could also include a voltage regulator to regulate the discharge voltage. If the device 10 is instead designed to discharge either alternating current or direct current, the power circuit 16 can be configured with a direct current branch electrically connecting the electrodes 12 with a direct current power source, and an alternating current branch for supplying the electrodes 12 with alternating current. The alternating current branch could either convert direct current power to alternating current, or electrically connect with an alternating current power source. The power circuit would also include a three state switch for de-energizing the electrodes 12, energizing the electrodes with direct current, or energizing the electrodes 12 with alternating current.

In operation, the user first places the electrodes 12 in contact with the target tissue. If the device 10 is provided with a casing 18 as described above, this can be accomplished by holding the body portion 22 of the casing 18 and placing the head portion 24 adjacent the target tissue. Once the electrodes 12 are positioned, the user laterally separates the electrodes 12 to place the tissue in tension. When the device 10 is provided with the electrode adjuster 46 described above, the user can laterally move the electrodes 12 by depressing the grip buttons 48 attached to the casing 18. Once the tissue is in tension, the user energizes the electrodes 12 for discharging an electric current to the targeted tissue.

In the preferred embodiment of the invention, the user can energize the electrodes 12 with either an internally mounted battery power supply 64 or an external alternating current source. To energize the electrodes from the battery power supply 64, the user depresses the power switch push button operator 80 until the battery is electrically engaged with the electrodes 12. The user will easily recognize battery engagement if the device 10 is provided with a battery power light 82. Otherwise, the user can touch the electrodes to determine if the battery power supply 64 is engaged. If the user prefers to energize the electrodes 12 with an external alternating current power source, the user can engage one end of a standard plug-in power cord within the receptacle 70, and engage the opposite end of the cord with the external power source. Typically, the power cord will have a plug disposed on the opposite end for engaging a standard wall outlet.

Once the tissue 34 is electrified for a sufficient period of time, the electrodes 12 are removed from the tissue surface and returned to their original position. In the preferred embodiment, the springs 56 of the adjustor 46 will urge the electrodes 12 into to their original position when the grip buttons 48 are released. The process can then be repeated at another targeted site.

In the above manner, the electrotherapy device tensions the tissue while an electric current is applied thereon. In doing so, the device separates tissue which has been folded together by wrinkles or sagging of the tissue. In addition, the tensioning process minimizes the distance, and therefore the electrical resistance, between the electrode and a target beneath the surface of the tissue. As a result, the electric current is encouraged to propagate into the depth of the tissue rather than across the surface of the tissue so that the beneficial effects of electrotherapy are enhanced.

Figures 7, 8:
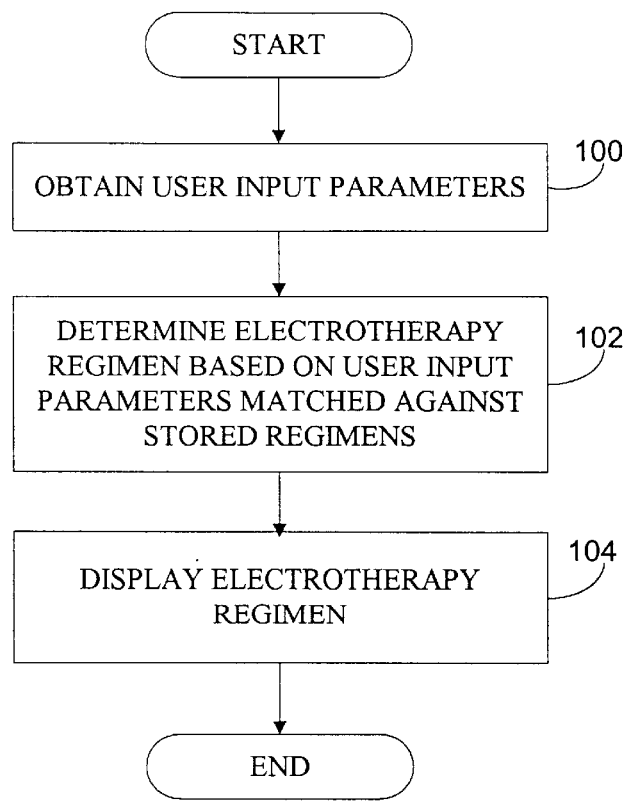
FIG. 7 is a flow diagram illustrating exemplary logic for providing a user with an electrotherapy regimen.
FIG. 8 illustrates exemplary user input parameters used in determining an electrotherapy regimen using the exemplary logic of FIG. 7.

Exemplary embodiments of the present invention include logic for providing a user with an electrotherapy regimen suitable for the user. For example, the electrotherapy regimen may be one designed to tone facial tissue and minimize wrinkling of the facial tissue. FIGS. 7–9 illustrate an exemplary embodiment for providing an electrotherapy regimen designed for a user's facial tissue.

FIG. 7 is a flow diagram illustrating exemplary logic for providing a user with an electrotherapy regimen. The logic of FIG. 7 may be executed on a microprocessor housed in the tissue tensioning electrotherapy device 10. Preferably, the logic of FIG. 10 is executed when a user turns on (powers on) the tissue tensioning therapy device 10. Also stored in the tissue tensioning electrotherapy device 10 is a database including tissue data. The tissue data includes preferred electrotherapy treatments that are based on various user parameters, for example, the age, gender, height, and skin type of the user.

The logic of FIG. 7 moves from a start block to block 100 where user input parameters are obtained. FIG. 8 illustrates exemplary user input parameters. In exemplary embodiments, one input parameter will be shown on display 90 at a time. Once the user selects an option for a given input parameter, the next input parameter and available selections will be shown. In exemplary embodiments, the user is first prompted to enter his or her gender. The user scrolls to the appropriate response (Male or Female) using buttons 88 on the tissue tensioning electrotherapy device 10. After selecting a gender, the user is prompted to select a race, such as Caucasian, Black, Hispanic or Asian. In exemplary embodiments, this parameter is optional and the user may opt to not select a race (e.g., by selecting No Answer). Next, the user is prompted to enter skin type (oily, normal or dry).

The user is then prompted to select his or her age from a list of age ranges, such as 20–29, 30–39, 40–49, 50–59 and 60+. Finally, the user is prompted to select the desired treatment area, for example, eyes, nose, cheekbones, mouth area, chin, upper arm, stomach or thighs.

In exemplary embodiments, a user can store his or her parameters so that the information does not have to be entered each time. Exemplary embodiments may allow for the storage of various sets of parameters for multiple users. For example, the first prompt may allow the user to select a set of stored parameters. For example, the stored parameters may be stored by number. Preferably, the stored parameters include everything but the treatment area. The user then selects the profile having his or her stored parameters (gender, race, skin type and age group) and the desired treatment area.

After the user's information (input parameters) has been obtained, the logic moves to block 102 where an electrotherapy regimen for the user is obtained by retrieving an appropriate regimen from the stored tissue data based on the information obtained from the user in block 100.

Next, the logic moves to block 104 where the electrotherapy regimen is displayed for the user. For example, the display may include where to place the tissue tensioning device 10, a mode of tissue tensioning electrotherapy and the amount of time for the tissue tensioning therapy. The display may also include how often the therapy should be performed (e.g., every day, every other day, twice a week, once a week, etc.).

While it is recognized that an illustrative and preferred embodiment has been described herein, it is likewise to be understood that the inventive concepts may be otherwise embodied and employed and that the appended claims are intended to be construed to include such variations except insofar as limited by the prior art.

What is claimed is:

1. A tissue tensioning electrostimulator device comprising:
  a) a plurality of laterally separable electrodes for placing bodily tissue in tension and for discharging electric current thereon;
  b) a power circuit in electrical communication with the electrodes and electrically connectable to a power supply;
  c) a tissue data repository configured to store a plurality of electrotherapy regimens, each electrotherapy regimen being associated with a plurality of user characteristics; and
  d) a microprocessor having logic for selecting an electrotherapy regimen for a user from the electrotherapy regimens stored in the tissue data repository.

2. The device as claimed in claim 1 further comprising an input device for obtaining user characteristics from the user.

3. The device as claimed in claim 2 wherein the user characteristics comprise age.

4. The device as claimed in claim 3 wherein the user characteristics comprise gender.

5. The device as claimed in claim 4 wherein the user characteristics comprise race.

6. The device as claimed in claim 5 wherein the user characteristics comprise skin type.

7. The device as claimed in claim 1 further comprising an output device for displaying the electrotherapy regimen selected for the user.

8. A method for determining a regimen for electrically stimulating body tissue, the method comprising the steps of:

a) obtaining a plurality of characteristics for a user;
b) selecting an electrotherapy regimen for the user based on the plurality of characteristics of the user;
c) displaying the selected electrotherapy regimen to the user;
d) placing the tissue in tension as provided in the selected electrotherapy regimen; and
e) applying an electric current to the tissue while the tissue is in tension.

9. The method as claimed in claim 9 wherein the user characteristics comprise age.

10. The method as claimed in claim 9 wherein the user characteristics comprise gender.

11. The method as claimed in claim 10 wherein the user characteristics comprise race.

12. The method as claimed in claim 11 wherein the user characteristics comprise skin type.

* * * * *